United States Patent
Yamamoto et al.

(10) Patent No.: US 6,403,852 B1
(45) Date of Patent: Jun. 11, 2002

(54) PROCESS FOR PRODUCING ALKENYL-SUBSTITUTED AROMATIC HYDROCARBONS

(75) Inventors: Michio Yamamoto, Otsu; Gohfu Suzukamo, Suita, both of (JP)

(73) Assignee: Sumitomo Chemical Co., Limited, Osaka-fu (JP)

( * ) Notice: Subject to any disclaimer, the term of this patent is extended or adjusted under 35 U.S.C. 154(b) by 0 days.

(21) Appl. No.: 09/331,804

(22) PCT Filed: Dec. 24, 1997

(86) PCT No.: PCT/JP97/04802

§ 371 (c)(1),
(2), (4) Date: Jun. 25, 1999

(87) PCT Pub. No.: WO98/29371

PCT Pub. Date: Jul. 9, 1998

(30) Foreign Application Priority Data

| Dec. 25, 1996 | (JP) | 8-346136 |
| Apr. 9, 1997 | (JP) | 9-090775 |
| Apr. 11, 1997 | (JP) | 9-093664 |
| Nov. 7, 1997 | (JP) | 9-305359 |
| Nov. 19, 1997 | (JP) | 9-318033 |
| Dec. 9, 1997 | (JP) | 9-338653 |

(51) Int. Cl.⁷ .......... C07C 15/46; C07C 1/207; C07C 15/067; C07C 2/64
(52) U.S. Cl. .......... 585/453; 585/438; 585/436; 585/452
(58) Field of Search .......... 585/438, 436, 585/452, 453; 502/344

(56) References Cited

U.S. PATENT DOCUMENTS

| 3,244,758 A | * | 4/1966 | Eberhardt | 585/320 |
| 4,990,717 A |   | 2/1991 | Sikkenga | 585/414 |
| 5,367,098 A |   | 11/1994 | Fushimi et al. | 585/452 |
| 3,650,704 A | * | 7/1995 | Kumura et al. | 423/415.1 |
| 5,436,381 A | * | 7/1995 | Takagawa et al. | 585/452 |
| 5,523,504 A |   | 6/1996 | Itoh | 585/451 |

FOREIGN PATENT DOCUMENTS

| EP | A1 0-612706 | | 8/1994 |
| JP | 0025-530 | * | 3/1975 |
| JP | 50-17975 | | 6/1975 |
| JP | 51-8930 | | 3/1976 |
| JP | 5-170674 A | | 7/1993 |
| JP | 6-293673 A | | 10/1994 |

* cited by examiner

*Primary Examiner*—Thuan D. Dang
(74) *Attorney, Agent, or Firm*—Birch, Stewart, Kolasch & Birch, LLP

(57) ABSTRACT

There are provided a process for producing an alkenyl-substituted aromatic hydrocarbon by alkenylation of an alkyl-substituted aromatic hydrocarbon having a hydrogen atom at the α-position of a side chain thereof with a conjugated diene, using a catalyst obtained by the action of an alkali metal compound and an alkali metal or an alkali metal hydroxide on an metal oxide selected from alumina or hydrotalcite by heating in a specific temperature range; and a process for producing an alkenyl-substituted aromatic hydrocarbon, characterized in that the reaction is carried out in the presence of an alkylaminopyridine of formula (1):

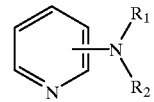

(1)

wherein $R_1$ is hydrogen or $C_1$–$C_6$ lower alkyl, and $R_1$ is $C_1$–$C_6$ lower alkyl, using as a catalyst, Na metal, K metal, or an alloy thereof, or a catalyst carrying any of them on an inorganic compound support, or a catalyst obtained by the action of an alkali metal compound and alkali metal or an alkali metal hydride on a metal oxide selected from alumina, alkaline earth metal oxides, hydrotalcite, silica-alumina, or zeolite by heating in a temperature range of 70° C. to 700° C.

13 Claims, No Drawings

PROCESS FOR PRODUCING ALKENYL-SUBSTITUTED AROMATIC HYDROCARBONS application is the national phase under 35 U.S.C. §371 of prior PCT International Application No. PCT/JP97/04802 which has an International filing date of Dec. 24, 1997 which designated the United States of America.

TECHNICAL FIELD

The present invention relates to a process for producing alkenyl-substituted aromatic hydrocarbons, in which an alkyl-substituted aromatic hydrocarbon having a hydrogen atom at the α-position of a side chain thereof is reacted with a conjugated diene using a catalyst, thereby causing alkenylation at the α-position.

BACKGROUND ART

Alkenyl-substituted aromatic hydrocarbons are useful as intermediate materials of fine chemicals such as agricultural chemicals, drugs, and chemical products, and also useful as the intermediate materials for the production of naphthalene derivatives. It is well known that they can be obtained by reacting an alkyl-substituted aromatic hydrocarbon having a hydrogen atom at the α-position of a side chain thereof with a conjugated diene in the presence of a basic catalyst.

For example, the following are such known processes:

a process using an alloy of sodium metal and potassium metal as the catalyst (see JP-B 50-17975 and JP-B 51-8930);

a process using a catalyst in which sodium metal is carried on a support obtained from aluminum hydroxide and potassium hydroxide (see JP-A 6-293673);

a process using a catalyst composed of an aromatic compound that forms a charge-transfer complex with sodium metal and an alkaline earth metal salt (see JP-B 8-59523); and a process in which a catalyst carrying an alkali metal on a support is filled in a reaction tube and production is achieved by flow-through reaction in a fixed-bed system (see U.S. Pat. No. 4,990,717).

The above catalysts and processes, however, have drawbacks that the rate of conversion of an alkyl-substituted aromatic hydrocarbon must be kept lower by reducing the amount of conjugated diene to be charged, relative to that of alkyl-substituted aromatic hydrocarbon, because of their low catalyst activity and insufficient selectivity.

The present inventors have extensively studied various alkenylation catalysts for the purpose of developing an excellent process for producing an alkenyl-substituted aromatic hydrocarbon by alkenylation at the α-position of a side chain of an alkyl-substituted aromatic hydrocarbon. As a result, they have found that a catalyst obtained by the action of an alkali metal compound and an alkali metal or an alkali metal hydride on a metal oxide selected from alumina or hydrotalcite by heating in a specific temperature range can exhibit remarkably high activity on alkenylation and provide a desired alkenyl-substituted aromatic hydrocarbon with high efficiency, even if the catalyst is used in a small amount.

The present inventors also have extensively studied various alkenylation catalysts and their additives for the purpose of developing a further excellent producing process. As a result, they have found that when the reaction is carried out in the presence of an alkylaminopyridine using an alkali metal or an alloy thereof, or a catalyst carrying any of them on an inorganic compound support, or a solid base catalyst obtained by the action of an alkali metal compound and an alkali metal or an alkali metal hydride on a metal oxide selected from alumina, alkaline earth metal oxides, hydrotalcite, silica-alumina, or zeolite by heating in a temperature range of 70° C. to 700° C., higher selectivity in alkenylation can be attained with the catalyst activity being retained, and a desired alkenyl-substituted aromatic hydrocarbon can be produced with high efficiency, even if the catalyst is used in a small amount. After further various studies, they have completed the present invention.

DISCLOSURE OF THE INVENTION

Thus, the present invention provides:

1. a process for producing an alkenyl-substituted aromatic hydrocarbon by alkenylation of an alkyl-substituted aromatic hydrocarbon having a hydrogen atom at the α-position of a side chain thereof with a conjugated diene, characterized in that the process involves the use of a catalyst selected from:

(1) a solid base catalyst obtained by the action of potassium hydroxide directly on alumina by heating in a temperature range of 300° C. to 600° C. and the subsequent action of sodium metal or sodium hydride on the alumina by heating in the same temperature range;

(2) a solid base catalyst obtained by the action of an alkali metal compound on alumina by heating and the subsequent action of potassium metal or potassium hydride on the alumina in an atmosphere of an inert gas by heating, both in a temperature range of 70° C. to 500° C.; or (3) a solid base catalyst obtained by the action of a potassium compound and sodium metal on hydrotalcite or by the action of a potassium compound and sodium hydride on hydrotalcite, both by heating in a temperature range of 100° C. to 700° C. in an atmosphere of an inert gas; and 2. a process for producing an alkenyl-substituted aromatic hydrocarbon by alkenylation of an alkyl-substituted aromatic hydrocarbon containing a hydrogen atom at the α-position of a side chain thereof with a conjugated diene, characterized in that the process involves the reaction in the presence of an alkylaminopyridine of formula (1):

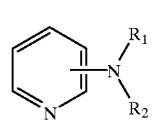

(1)

wherein $R_1$ is hydrogen or $C_1$–$C_6$ lower alkyl, and $R_2$ is $C_1$–$C_6$ lower alkyl, using as a catalyst, Na metal, K metal, or an alloy thereof, or a catalyst carrying any of them on an inorganic compound support, or a catalyst obtained by the action of an alkali metal compound and an alkali metal or an alkali metal hydride on a metal oxide selected from alumina, alkaline earth metal oxides, hydrotalcite, silica-alumina, or zeolite by heating in a temperature range of 70° C. to 700° C.

The present invention will hereinafter be explained in detail.

First, the following will describe the first embodiment of the present invention, i.e., a process for producing an alkenyl-substituted aromatic hydrocarbon by alkenylation of an alkyl-substituted aromatic hydrocarbon having a hydrogen atom at the α-position of a side chain thereof with a conjugated diene, using a catalyst obtained by the action of an alkali metal compound and an alkali metal or an alkali metal hydroxide on an metal oxide selected from alumina or hydrotalcite by heating in a specific temperature range.

Examples of the alkyl-substituted aromatic hydrocarbon having a hydrogen atom at the α-position of a side chain thereof, which are usually used, may include monocyclic aromatic hydrocarbons and condensed polycyclic aromatic hydrocarbons. The side chain alkyl group may be combined together to form a ring.

Specific examples of the alkyl-substituted aromatic hydrocarbon having a hydrogen atom at the α-position of a side chain thereof are toluene, ethylbenzene, isopropylbenzene, n-propylbenzene, n-butylbenzene, secbutylbenzene, isobutylbenzene, xylene, cymene, diisopropylbenzene, methyl-naphthalene, tetrahydronaphthalene, and indane. Preferably used are toluene, xylene, and ethylbenzene.

Examples of the conjugated diene, which are usually used, may include those having about 4 to about 10 carbon atoms, and they may be either in straight chain form or in branched form.

Specific examples of the conjugated diene are 1,3-butadiene, 2-methyl-1,3-butadiene, 1,3-pentadiene, and 1,3-hexadiene. Preferably used are 1,3-butadiene and 2-methyl-1,3-butadiene.

Examples of the catalyst, which can be used in the alkenylation of the present invention, may include catalysts (solid base catalysts) obtained by the action of an alkali metal compound and an alkali metal, or by the action of an alkali metal compound and an alkali metal hydride on a metal oxide selected from alumina or hydrotalcite.

The following will describe the solid base catalyst.

Examples of the solid base catalyst may include:

(1) a solid base catalyst obtained by the action of potassium hydroxide directly on alumina by heating in a temperature range of 300° C. to 600° C. in the air or under an atmosphere of an inert gas and the subsequent action of sodium metal or sodium hydride on the alumina by heating in a temperature range of 305° C. to 550° C. under an atmosphere of an inert gas, wherein the amount of potassium hydroxide to be used is 5% to 50% by weight, relative to the alumina, and the amount of sodium metal to be used is 2% to 15% by weight;

(2) a solid base catalyst obtained by the action of an alkali metal compound on alumina by heating in a temperature range of 200° C. to 500° C. in the air or under an atmosphere of an inert gas and the subsequent action of potassium metal or potassium hydride on the alumina by heating in a temperature range of 70° C. to 40° C. in an atmosphere of an inert gas, wherein the amount of alkali metal compound to be used is 5% to 70% by weight, preferably 10% to 50% by weight, relative to the alumina, and the amount of potassium metal or potassium hydride to be used is 2% to 10% by weight, relative to the alumina; and (3) a solid base catalyst obtained by the action of a potassium compound and sodium metal on hydrotalcite or by the action of a potassium compound and sodium hydride on hydrotalcite, both by heating in a temperature range of 100° C. to 700° C. in an atmosphere of an inert gas. Potassium compound may be reacted in a temperature range of 200° C. to 600° C.

Specific examples of the sodium compound are sodium hydroxide, sodium carbonate, sodium hydrogencarbonate, and sodium alkoxide.

The amount of alkali metal compound to be used is usually in the range of 5% to 70%, relative to the support.

In usual cases, an alkali metal compound is preferably allowed to act directly on a support just as it is in powder or flake form; however, it may also be dissolved or suspended in water or an organic solvent, followed by the addition to a support and the action by heating at a prescribed temperature. These steps may be performed in the air, or if required, under an atmosphere of an inert gas.

Examples of the alkali metal, which are preferably used, may include sodium metal, potassium metal, and alloys of sodium and potassium. In this case, of a preferred combination of a potassium compound and sodium metal or sodium hydride, or a combination of a sodium compound and potassium metal or potassium hydride; particularly preferred is a combination of a potassium compound and sodium metal and sodium hydride.

The alkali metal or alkali metal hydride is preferably used under an atmosphere of an inert gas, examples of which are nitrogen gas, helium gas, and argon gas.

The amount of alkali metal or alkali metal hydroxide to be used is usually in the range of 2% to 20%, relative to the support.

In the preparation of such a solid base catalyst, the heating time may vary depending upon the selected conditions; however, the action time is in the range of 0.5 to 10 hours for alkali metal compounds or 0.1 to 5 hours for alkali metals or alkali metal hydrides.

Thus, the solid base catalyst can be obtained, which has good fluidity and good operability, as well as extremely excellent activity on the desired reaction.

The reaction temperature is usually in the range of about 0° C. to about 200° C., preferably about 50° C. to about 180° C. The reaction pressure is usually in the range of about atmospheric pressure to about 20 kg/cm$^2$, preferably about atmospheric pressure to about 5 kg/cm$^2$.

The mole ratio of conjugated diene to alkyl-substituted aromatic hydrocarbon having a hydrogen atom at the α-position of a side chain thereof is usually in the range of about 0.01 to about 1, preferably about 0.05 to about 0.8.

The amount of catalyst to be used in a batch system is usually about 0.01% to about 20% by weight, preferably about 0.1% to about 10% by weight, relative to the aromatic hydrocarbon used. The reaction time is usually in the range of about 0.1 to about 50 hours, preferably about 0.5 to about 25 hours.

The total rate of supply of an alkyl-substituted aromatic hydrocarbon having a hydrogen atom at the α-position of a side chain thereof plus a conjugated diene in the flow-through reaction is usually about 0.01 to about 100 hr$^{-1}$, preferably about 0.1 to about 20 hr$^{-1}$, in LHSV.

The following will describe the second embodiment of the present invention, i.e., a process for producing an alkenyl-substituted aromatic hydrocarbon by alkenylation of an alkyl-substituted aromatic hydrocarbon having a hydrogen atom at the α-position of a side chain thereof with a conjugated diene, characterized in that the reaction is carried out in the presence of an alkylaminopyridine of formula (1):

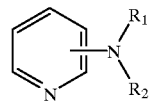

(1)

wherein $R_1$ is hydrogen or $C_1$–$C_6$ lower alkyl, and $R_1$ is $C_1$–$C_6$ lower alkyl, using as a catalyst, Na metal, K metal, or an alloy thereof, or a catalyst carrying any of them on an inorganic compound support, or a catalyst obtained by the action of an alkali metal compound and an alkali metal or an alkali metal hydride on a metal oxide selected from alumina, alkaline earth metal oxides, hydrotalcite, silica-alumina, or zeolite by heating in a temperature range of 70° C. to 700° C.

The alkyl-substituted aromatic hydrocarbon having a hydrogen atom at the α-position of a side chain thereof and the conjugated diene, which are used in this embodiment, may include those which are the same as used in the above first embodiment.

In this embodiment, Na metal, K metal, or alloys thereof, can be used as the catalyst. Preferably used are alloys of sodium and potassium at a weight ratio of 1:1 to 10:1. The amount of such a catalyst to be used is usually in the range of 0.01% to 10% by weight, preferably 0.03% to 5% by weight, relative to the alkyl-substituted aromatic hydrocarbon having a hydrogen atom at the α-position of a side chain thereof.

Examples of the inorganic compound, which are preferably used for carrying Na metal, K metal, or an alloy thereof, may include potassium carbonate and metal oxides, particularly alumina, magnesium oxide, calcium oxide, hydrotalcite, zeolite, and potassium carbonate. The amount of Na metal, K metal, or an alloy thereof to be used is usually in the range of 1% to 20% by weight, preferably 2% to 12% by weight, relative to the support.

The catalyst carrying Na metal, K metal, or an alloy thereof on an inorganic compound support is obtained by the action of both by heating in a temperature range of a melting point thereof to 500° C., preferably 100° C. to 400° C., under an atmosphere of an inert gas such as nitrogen gas.

In the second embodiment of the present invention, besides Na metal, K metal, alloys thereof, and catalysts carrying any of them on an inorganic compound support, as described above, there can also be used a catalyst which is obtained by the action of an alkali metal compound and an alkali metal or an alkali metal hydride on a metal oxide selected from alumina, alkaline earth metal oxides, hydrotalcite, silica-alumina, or zeolite in a temperature range of 70° C. to 700° C. Examples of the alkaline earth metal oxide, which are preferably used, may include magnesium oxide, calcium oxide, and barium oxide. With the use of such a catalyst in the presence of an alkylaminopyridine of formula (1) as depicted above, the alkenylation can be carried out.

In the alkylaminopyridine of formula (1), the $C_1$–$C_6$ lower alkyl, which is represented by $R_1$ or $R_2$, may include methyl, ethyl, propyl, butyl, pentyl, and hexyl.

Examples of the alkylaminopyridine of formula (1) are dimethylaminopyridine, diethylaminopyridine, dipropylaminopyridine, dibutylaminopyridine, methylethylaminopyridine, methylpropylaminopyridine, methylbutylaminopyridine, methylaminopyridine, ethylaminopyridine, propylaminopyridine, and butylaminopyridine. These may be used in form just as it is commercially available, or if necessary, purified by distillation, recrystallization, or dehydration.

The amount of alkylaminopyridine to be added is usually in the range of 0.001% to 1.0% by weight, preferably 0.01% to 0.3% by weight, relative to the alkyl-substituted aromatic hydrocarbon having a hydrogen atom at the α-position of a side chain thereof.

In the process of the present invention, the alkenylation can be carried out using a catalyst such as described above, either in a batch system or in a flow-through system with a fluidized or fixed bed.

The reaction temperature is usually in the range of about 0° C. to about 200° C., preferably about 50° C. to about 180° C. The reaction pressure is usually in the range of about atmospheric pressure to about 20 kg/cm², preferably about atmospheric pressure to about 5 kg.cm².

The mole ratio of conjugated diene to alkyl-substituted aromatic hydrocarbon having a hydrogen atom at the α-position of a side chain thereof is usually in the range of about 0.01 to about 1, preferably about 0.05 to about 0.8.

The amount of catalyst to be used in a batch system is usually about 0.01% to about 20% by weight, preferably about 0.1% to about 10% by weight, relative to the aromatic hydrocarbon used. The reaction time is usually in the range of about 0.1 to about 50 hours, preferably about 0.5 to about 25 hours.

The total rate of supply of an alkyl-substituted aromatic hydrocarbon having a hydrogen atom at the α-position of a side chain thereof plus a conjugated diene in the flow-through reaction is usually about 0.01 to about 100 $hr^{-1}$, preferably about 0.1 to about 20 $hr^{-1}$, in LHSV.

EFFECTS OF THE INVENTION

Thus, the alkenyl-substituted aromatic hydrocarbon is produced. According to the present invention, the desired alkenyl-substituted aromatic hydrocarbons can be produced with extremely high efficiency, even if the catalyst is used in a small amount, and even under mild conditions.

In addition, the handling of a catalyst and the treatment after the reaction are quite easy, so that the present invention is also advantageous in this regard.

EXAMPLES

The present invention will be further illustrated by the following examples; it should, however, be understood that the present invention is not limited to these examples.

Preparation of Catalysts (Solid Base A)

First, 25 g of active alumina (Sumitomo Chemical Company, Limited) adjusted to have the particle size ranging from 100 to 200 mesh was stirred at 500° C. under an atmosphere of nitrogen gas for 1 hour, and then cooled to 350° C., followed by the addition of 5.88 g of potassium hydroxide and stirring at the same temperature for 3 hours.

The mixture was then cooled to 310° C., followed by the addition of 2.05 g of sodium metal and stirring at the same temperature for 0.5 hour. The resulting mixture was let stand for cooling to room temperature to give solid base A.

(Solid Base B)

Solid base B was prepared by the same procedures as used in the preparation of solid base A, except that potassium hydroxide and sodium metal were used in amounts of 4.41 g and 1.45 g, respectively.

(Solid Base C)

Solid base C was prepared by the same procedures as used in the preparation of solid base A, except that potassium hydroxide and sodium metal were used in amounts of 4.41 g and 2.3 g, respectively.

(Solid Base D)

Solid base D was prepared by the same procedures as used in the preparation of solid base A, except that potassium hydroxide was not used and sodium metal was used in an amount of 2.3 g.

(Solid Base E)

Solid base E was prepared by the same procedures as used in the preparation of solid base A, except that potassium hydroxide was not used and sodium metal was used in an amount of 1.54 g.

(Solid Base F)

Solid base F was prepared by the same procedures as used in the preparation of solid base A, except that potassium hydroxide was not used and potassium metal was used in an amount of 1.54 g.

(Solid Base G)

Solid base G was prepared by the same procedures as used in the preparation of solid base A, except that 4.41 g of sodium hydroxide was substituted for potassium hydroxide and sodium metal was used in an amount of 1.45 g.

(Solid Bases H to J)

Solid bases H to J were prepared by the same procedures as used in the preparation of solid base A, except that the temperature for the addition of sodium metal and the subsequent stirring was changed to 500° C., 400° C., and 110° C., respectively.

(Solid Base K)

Solid base K was prepared by the same procedures as used in the preparation of solid base A, except that 3.57 g of sodium hydride (60% content) was substituted for sodium metal.

Example 1

Into a 1000-mL autoclave with a magnetic stirrer was charged 1.0 g of solid base A and 220 g of o-xylene, and the mixture was heated to 140° C. under stirring at 700 r.p.m., to which 16.5 g of butadiene was then supplied at the same temperature for 1 hour.

After the reaction, the autoclave was cooled, and the catalyst was filtered out. The reaction mixture was then analyzed by gas chromatography. The yield of 5-tolylpentene-2 to the consumed o-xylene was 89%.

Examples 2, 3, and Comparative Examples 1 to 4

The reaction was carried out in the same manner as described in Example 1, except that solid bases B, C, D, E, F, and G were substituted for solid base A, respectively, The results are shown in Table 1.

Comparative Example 5, 6, and 7

The reaction was carried out in the same manner as described in Example 1, except that 0.06 g of sodium metal, 0.06 g of 5:1 Na—K alloy, and solid base J were substituted for solid base A, respectively. The results are shown in Table 1.

TABLE 1

|  | Catalyst | Yield (%) |
| --- | --- | --- |
| Example 1 | A | 89 |
| Example 2 | B | 88 |
| Example 3 | C | 87 |
| Comparative Example 1 | D | 51 |
| Comparative Example 2 | E | 49 |
| Comparative Example 3 | F | 0 |
| Comparative Example 4 | G | 0 |
| Comparative Example 5 | Na | 47 |
| Comparative Example 6 | Na—K | 65 |
| Comparative Example 7 | J | 75 |

Examples 4 to 6

The reaction was carried out in the same manner as described in Example 1, except that 182g of toluene, 210 g of ethylbenzene, and 238 g of cumene were substituted for o-xylene to give 5-phenylpentene-2, 5-phenylhexene-2, and 5-methyl-5-phenylhexene-2, respectively. The results are shown in Table 2.

Example 7

The reaction was carried out in the same manner as described in Example 1, except that 19 g of isoprene was substituted for butadiene to give 3-methyl-5-tolylpentene-2. The results are shown in Table 2.

Examples 8 to 10

The reaction was carried out in the same manner as describe din Example 1, except that solid bases H, I, and K were substituted for solid base A, respectively. The results are shown in Table 2.

TABLE 2

|  | Solid Base | Yield (%) |
| --- | --- | --- |
| Example 4 | A | 90 |
| Example 5 | A | 92 |
| Example 6 | A | 59 |
| Example 7 | A | 92 |
| Example 8 | H | 89 |
| Example 9 | I | 89 |
| Example 10 | K | 79 |

Preparation of Catalysts (Solid Base L)

First, 25 g of active alumina (Sumitomo Chemical Company, Limited) adjusted to have the particle size ranging from 100 to 200 mesh was stirred at 500° C. under an atmosphere of nitrogen gas for 1 hour, and then cooled to 310° C., followed by the addition of 12.5 g of sodium hydroxide and stirring at the same temperature for 3 hours.

The mixture was then cooled to 200° C., followed by the addition of 1.5 g of potassium metal and stirring at the same temperature for 0.5 hour. The resulting mixture was let stand for cooling to room temperature to give solid base L.

(Solid Base M)

Solid base M was prepared by the same procedures as used in the preparation of solid base L, except that the amount of sodium hydroxide to be added was changed to 7.5 g.

(Solid Base N)

Solid base N was prepared by the same procedures as used in the preparation of solid base L, except that the temperature for the addition of potassium metal was changed to 110° C.

(Solid Base O)

Solid base O was prepared by the same procedures as used in the preparation of solid base L, except that 14.7 g of potassium hydroxide was substituted for sodium hydroxide and the subsequent stirring was carried out at 350° C. for 3 hours.

(Solid Bases P and Q)

Solid bases P and Q were prepared by the same procedures as used in the preparation of solid base L, except that the temperature for the addition of potassium metal was changed to 300° C. and 400° C., respectively.

(Solid Bases R, S, and T)

Solid bases R, S, and T were prepared by the same procedures as used in the preparation of solid base L, except that sodium hydroxide was not added and the temperature for the addition of potassium metal was changed to 110° C., 200° C., and 300° C.
(Solid Base U)

Solid base U was prepared by the same procedures as used in the preparation of solid base O, except that the temperature for the addition of potassium metal was changed to 550° C.

Example 11

Into a 1000-mL autoclave with a magnetic stirrer was charged 1.0 g of solid base L and 220 g of o-xylene, and the mixture was heated to 140° C. under stirring at 700 r.p.m., to which 16.5 g of butadiene was then supplied at the same temperature for 1 hour.

After the reaction, the autoclave was cooled, and the catalyst was filtered out. The reaction mixture was then analyzed by gas chromatoraphy. The yield of 5-tolylpentene-2 to the consumed o-xylene was 86%.

Examples 12 to 16

The reaction was carried out in the same manner as described in Example 11, except that solid bases M, N, O, P, and Q were substituted for solid base L, respectively. The results are shown in Table 3.

Comparative Examples 8 to 11

The reaction was carried out in the same manner as described in Example 11, except that solid bases R, S, T, and U were substituted for solid base L, respectively. The results are shown in Table 3.

TABLE 3

|  | Solid Base | Yield (%) |
| --- | --- | --- |
| Example 11 | L | 86 |
| Example 12 | M | 84 |
| Example 13 | N | 83 |
| Example 14 | O | 85 |
| Example 15 | P | 86 |
| Example 16 | Q | 83 |
| Comparative Example 8 | R | 58 |
| Comparative Example 9 | S | 5 |
| Comparative Example 10 | T | 0 |
| Comparative Example 11 | U | 29 |

Preparation of Catalysts
(Solid Base V)

First, 25 g of synthetic hydrotalcite KW-10000 (Kyowa Chemical Industry, Co., Ltd.) was stirred at 500° C. under an atmosphere of nitrogen gas for 1 hour, and then cooled to 350° C., followed by the addition of 4.4 g of potassium hydroxide and stirring at the same temperature for 3 hours.

The mixture was then cooled to 310° C., followed by the addition of 1.5 g of sodium metal and stirring at the same temperature for 0.5 hour. The resulting mixture was let stand for cooling to room temperature to give solid base V.
(Solid Base W)

Solid base W was prepared by the same procedures as used in the preparation of solid base V, except that potassium hydroxide and sodium metal were used in amounts of 4.4 g and 1.0 g, respectively.
(Solid Base X)

Solid base X was prepared by the same procedures as used in the preparation of solid base V, except that potassium hydroxide was not added.

Example 17

Into a 1000-mL autoclave with a magnetic stirrer was charged 1.0 g of solid base V and 220 g of o-xylene, and the mixture was heated to 140° C. under stirring at 700 r.p.m., to which 16.5 g of butadiene was then supplied at the same temperature for 1 hour.

After the reaction, the autoclave was cooled, and the catalyst was filtered out. The reaction mixture was then distilled for separation into the product and the unreacted o-xylene. The results are shown in Table 4.

Example 18

The reaction was carried out in the same manner as described in Example 17, except that solid base W was substituted for solid base V. The results are shown in Table 4.

Comparative Example 12

The reaction was carried out in the same manner as described in Example 17, except that solid base X was substituted for solid base V. The results are shown in Table 4.

TABLE 4

|  | Catalyst | Yield (%) |
| --- | --- | --- |
| Example 17 | solid base V | 84 |
| Example 18 | solid base W | 82 |
| Comparative Example 12 | solid base X | 49 |
| Comparative Example 5 | sodium metal | 47 |

Example 19

Into a 300-mL 4-necked glass flask equipped with a magnetic stirrer, a thermometer, and a condenser, as a reaction apparatus, was charged 100 g of o-xylene, 1.0 g of solid base D, and 0.05 g of 4-dimethylaminopyridine under an atmosphere of nitrogen gas, and the mixture was heated to 135 ° C. under stirring at 600 r.p.m., to which 8 g of butadiene was then supplied at the same temperature for 1.5 hour. After the reaction, the apparatus was cooled, and the catalyst was filtered out. The reaction mixture was then analyzed by gas chromatography. The yield of 5-tolylpentene-2 to the consumed o-xylene was 87%.

Comparative Example 13

The reaction was carried out in the same manner as described in Example 19, except that 0.05 g of 4-dimethylaminopyridine was not added. The yield of 5-tolylpentene-2 to the consumed o-xylene was 61%.

Example 20

The reaction was carried out in the same manner as described in Example 19, except that 2-dimethylaminopyridine was substituted for 4-dimethylaminopyridine. The yield of 5-tolylpentene-2 to the consumed o-xylene was 86%.

Example 21

The reaction was carried out in the same manner as described in Example 19, except that 2-methylaminopyridine was substituted for 4-dimethylaminopyridine. The yield of 5-tolylpentene-2 to the consumed o-xylene was 89%.

Example 22

The reaction was carried out in the same manner as described in Example 19, except that ethylbenzene was substituted for o-xylene; and solid base A, for solid base D; the amount of butadiene to be supplied was changed from 8 g to 25 g; the supply time, from 1.5 hours to 3 hours; and the reaction temperature, from 135° C. to 120° C. After the reaction, the catalyst was filtered out, and the filtrate was then distilled to give 37 g of 5-phenylhexene-2.

Comparative Example 14

The reaction was carried out in the same manner as described in Example 22, except that 0.05 g of 4-dimethylaminopyridine was not added. After the reaction, the catalyst was filtered out, and the filtrate was then distilled to give 28 g of 5-phenylhexene-2.

Example 23

The reaction was carried out in the same manner as described in Example 22, except that the reaction temperature was changed from 120° C. to 80° C. After the reaction, the catalyst was filtered out, and the filtrate was then distilled to give 26 g of 5-phenylhexene-2.

Comparative Example 15

The reaction was carried out in the same manner as described in Example 23, except that 0.05 g of 4-dimethylaminopyridine was not added. After the reaction, the catalyst was filtered out, and the filtrated was then distillated to give 12 g of 5-phenylhexene-2.

Example 24

The reaction was carried out in the same manner as described in Example 22, except that 0.6 g of Na—K alloy (5:1 weight ratio) was substituted for solid base B and the reaction temperature was changed from 120° C. to 130° C. After the reaction, the catalyst was filtered out, and the filtrate was then distilled to give 37 g of 5-phenylhexene-2.

Comparative Example 16

The reaction was carried out in the same manner as described in Example 24, except that 0.05 g of 4-dimethylaminopyridine was not added. After the reaction, the catalyst was filtered out, and the filtrate was distilled to give 29 g of 5-phenylhexene-2.

What is claimed is:

1. A process for producing an alkenyl-substituted aromatic hydrocarbon which comprises:
    alkenylating an alkyl-substituted aromatic hydrocarbon having a hydrogen atom at an α-position of a side chain thereof with a conjugated diene, in the presence of a catalyst selected from the group consisting of:
    (1) a solid base catalyst obtained by the steps of:
        (a) reacting an alkali metal compound selected from the group consisting of potassium hydroxide, potassium carbonate, potassium hydrogencarbonate, potassium alkoxide, a potassium salt of an organic acid, sodium hydroxide, sodium carbonate, sodium hydrogencarbonate, and sodium alkoxide, with alumina by heating in a temperature range of 70° C. to 500° C., and
        (b) reacting the resulting mixture from step (a) with potassium metal or potassium hydride in an inert gas atmosphere by heating in a temperature range of 70° C. to 500° C.; and
    (2) a solid base catalyst obtained by the step of reacting
        (i) a potassium compound selected from the group consisting of potassium hydroxide, potassium carbonate, potassium hydrogencarbonate, potassium alkoxide, and a potassium salt of an organic acid, and
        (ii) sodium metal or sodium hydride with hydrotalcite by heating in a temperature range of 100° C. to 700° C. in an inert gas atmosphere.

2. A process for producing an alkenyl-substituted aromatic hydrocarbon which comprises:
    alkenylating an alkyl-substituted aromatic hydrocarbon containing a hydrogen atom at an α-position of a side chain thereof with a conjugated diene, in the presence of a solid base catalyst obtained by the steps of:
    (a) reacting an alkali metal compound selected from the group consisting of potassium hydroxide, potassium carbonate, potassium hydrogencarbonate, potassium alkoxide, a potassium salt of an organic acid, sodium hydroxide, sodium carbonate, sodium hydrogencarbonate, and sodium alkoxide, with alumina by heating in a temperature range of 70° C. to 500° C., and
    (b) reacting the resulting mixture from step (a) with potassium metal or potassium hydride in an inert gas atmosphere by heating in a temperature range of 70° C. to 500° C.

3. The process according to claim 2, wherein the reaction temperature in step (a) is in a range of 200° C. to 500° C.

4. The process according to claim 2, wherein the reaction temperature in step (b) is in a range of 70° C. to 400° C.

5. The process according to claim 2, 3, or 4, wherein the amount of potassium metal or potassium hydride to be used is in the range of 2% to 10% by weight, relative to the alumina.

6. A process for producing an alkenyl-substituted aromatic hydrocarbon which comprises:
    alkenylating an alkyl-substituted aromatic hydrocarbon containing a hydrogen atom at an α-position of a side chain thereof with a conjugated diene, in the presence of a solid base catalyst obtained by the steps of:
    (a) reacting a potassium compound selected from the group consisting of potassium hydroxide, potassium carbonate, potassium hydrogencarbonate, potassium alkoxide, and a potassium salt of an organic acid, with hydrotalcite by heating in a temperature range of 100° C. to 700° C., and
    (b) reacting the resulting mixture with sodium metal or sodium hydride in an inert gas atmosphere by heating in a temperature range of 100° C. to 700° C.

7. The process according to claim 6, wherein the potassium compound is reacted in a temperature range of 200° C. to 600° C.

8. The process according to claim 6 or 7, wherein the amount of sodium metal or sodium hydride is in the range of 2% to 10% by weight, relative to the hydrotalcite.

9. A process for producing an alkenyl-substituted aromatic hydrocarbon which comprises:
    alkenylating an alkyl-substituted aromatic hydrocarbon containing a hydrogen atom at an α-position of a side chain thereof with a conjugated diene in the presence of an alkylaminopyridine of formula (1):

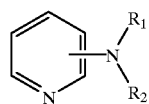 (1)

wherein $R_1$ is a hydrogen atom or $C_1$–$C_6$ lower alkyl group, and $R_2$ is $C_1$–$C_6$ lower alkyl group, and
a solid base catalyst selected from the group consisting of:
  (a) a sodium metal, a potassium metal, an alloy thereof or a catalyst carrying any of the sodium metal, the potassium metal and the alloy thereof on an inorganic compound support,
  (b) a catalyst obtained by reacting
    (i) an alkali metal compound selected from the group consisting of potassium hydroxide, potassium carbonate, potassium hydrogencarbonate, potassium alkoxide, a potassium salt of an organic acid, sodium hydroxide, sodium carbonate, sodium hydrogencarbonate and sodium alkoxide, and
    (ii) an alkali metal or an alkali metal hydride, with a metal oxide selected from the group consisting of alumina, alkaline earth metal oxides, hydrotalcite, silica-alumina and zeolite,
in a temperature range of 70° C. to 700° C.

10. The process according to claim 9, wherein the catalyst is the catalyst as defined in (a).

11. The process according to claim 9 or 10, wherein the catalyst is the one obtained by reacting the sodium metal, the potassium metal, or the alloy thereof on the inorganic compound support in a range of a melting point of the metal to 500° C.

12. The process according to claim 1, 2, 3, 4, 9, or 10, wherein the alkenylation is carried out in a temperature range of 50° C. to 180° C.

13. The process according to claim 9, wherein the solid base catalyst in (b) is the catalyst obtained by the steps of:
  (a) reacting
    (i) a potassium compound selected from the group consisting of potassium hydroxide, potassium carbonate, potassium hydrogencarbonate, potassium alkoxide, and a potassium salt of an organic acid, with (ii) a metal oxide selected from the group consisting of alumina, alkaline earth metal oxides, hydrotalcite, silica-alumina and zeolite, by heating in a temperature range of 70° C. to 700° C.; and
  (b) reacting the resulting mixture with an alkali metal or an alkali metal hydride.

\* \* \* \* \*